United States Patent

(12) United States Patent
Allen et al.

(10) Patent No.: US 12,260,405 B1
(45) Date of Patent: *Mar. 25, 2025

(54) PAYMENT CARD RECONCILIATION BY AUTHORIZATION CODE

(71) Applicant: VPay, Inc., Plano, TX (US)

(72) Inventors: Robert M. Allen, Plano, TX (US); Richard A. Maxwell, Plano, TX (US)

(73) Assignee: VPAY, INC., Plano, TX (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/901,409

(22) Filed: Sep. 1, 2022

Related U.S. Application Data

(63) Continuation of application No. 16/914,600, filed on Jun. 29, 2020, now Pat. No. 11,468,442, which is a continuation of application No. 15/131,742, filed on Apr. 18, 2016, now Pat. No. 10,740,755, which is a continuation of application No. 14/843,508, filed on Sep. 2, 2015, now abandoned.

(60) Provisional application No. 62/044,446, filed on Sep. 2, 2014.

(51) Int. Cl.
G06Q 20/40 (2012.01)
G06Q 20/10 (2012.01)
G06Q 20/34 (2012.01)
G06Q 50/22 (2024.01)

(52) U.S. Cl.
CPC .......... *G06Q 20/40* (2013.01); *G06Q 20/102* (2013.01); *G06Q 20/351* (2013.01); *G06Q 20/4018* (2013.01); *G06Q 50/22* (2013.01)

(58) Field of Classification Search
None
See application file for complete search history.

(56) References Cited

U.S. PATENT DOCUMENTS 5,590,196 A 12/1996 Moreau
5,677,955 A 10/1997 Doggett et al.
5,832,460 A 11/1998 Bednar et al.
(Continued)

FOREIGN PATENT DOCUMENTS

EP 1049056 A2 11/2000

OTHER PUBLICATIONS

Anthem, "835 Claim Payment/Advice," Release 1 (Mar. 2009), Version 004010A1—Oct. 2002 (Year: 2009).*
(Continued)

*Primary Examiner* — Peter H Choi
*Assistant Examiner* — John P Go
(74) *Attorney, Agent, or Firm* — Alston & Bird LLP

(57) ABSTRACT

A payment processor acting on behalf of a third party administrator to make payment on an adjudicated claim makes a straight through payment to an acquirer for a health care provider's merchant account. Via the authorization process, the payment processor generates an authorization code which is returned to the health care provider on its merchant statement for the payment. Concurrently, the remittance advice from the third party administrator is linked to the same authorization code as the payment by the payment processor which sends the advice in an 835-formatted transmission to the health care provider. Thus, the remittance advice may be linked (reconciled) with the payment on the merchant statement by the common authorization code.

19 Claims, 3 Drawing Sheets

(56) References Cited

U.S. PATENT DOCUMENTS

| | | | |
|---|---|---|---|
| 5,890,129 | A | 3/1999 | Spurgeon |
| 6,003,007 | A | 12/1999 | Dirienzo |
| 6,901,387 | B2 | 5/2005 | Wells et al. |
| 7,380,707 | B1 | 6/2008 | Fredman |
| 7,752,134 | B2 | 7/2010 | Spear |
| 7,792,686 | B2 * | 9/2010 | Allen ................ G06Q 40/08 709/200 |
| 8,204,766 | B2 | 6/2012 | Bush |
| RE43,904 | E | 1/2013 | Allen |
| 8,504,428 | B1 | 8/2013 | Houghtaling |
| RE44,748 | E | 2/2014 | Allen |
| 10,740,755 | B2 | 8/2020 | Allen et al. |
| 11,468,442 | B1 | 10/2022 | Allen et al. |
| 2001/0034618 | A1 | 10/2001 | Kessler et al. |
| 2002/0194027 | A1 | 12/2002 | Smith |
| 2004/0249745 | A1 | 12/2004 | Baaren |
| 2005/0033604 | A1 | 2/2005 | Hogan |
| 2005/0209964 | A1 | 9/2005 | Allen et al. |
| 2005/0261944 | A1 | 11/2005 | Rosenberger |
| 2006/0010016 | A1 | 1/2006 | Kossol et al. |
| 2007/0005402 | A1 | 1/2007 | Kennedy et al. |
| 2008/0017704 | A1 | 1/2008 | Vandeburg et al. |
| 2008/0077438 | A1 * | 3/2008 | Yanak ................ G06Q 20/108 705/2 |
| 2008/0133266 | A1 | 6/2008 | Allen |
| 2009/0222353 | A1 | 9/2009 | Guest et al. |
| 2011/0258004 | A1 * | 10/2011 | Dean ................ G06Q 10/10 705/4 |
| 2012/0035952 | A1 * | 2/2012 | Coyne ................ G06Q 40/08 705/2 |
| 2016/0063201 | A1 | 3/2016 | Allen et al. |

OTHER PUBLICATIONS

"AP vPayment XML Supplier Training", GE Corporate Payment Services, dated Jan. 26, 2005.

Anthem, "835 Claim Payment/Advice," Mar. 2009, pp. 1-14.

Anthem, "837 Professional Health Care Claim," Feb. 2011, pp. 1-23.

Decision Denying Institution of Covered Business Method Patent Review, Case CBM2013-00047 U.S. Pat. No. Re. 43,904, Entered: Feb. 18, 2014, pp. 1-24.

Decision Denying Institution of Inter Partes Review, Case !PR2014-01414 U.S. Pat. No. Re. 43,904 E, Entered: Mar. 4, 2015, pp. 1-24.

Decision Institution of Inter Partes Review Case, IPR2015-00569 U.S. Pat. No. Re. 44,748 E, Entered: Jul. 31, 2015, pp. 1-36.

District Court's Order responsive to Motion for Summary Judgment in CA No. 8:13-cv-2240-T-33MAP pp. 1-30.

Joint Claim Construction and Prehearing Statement, *Stoneeagle Services, Inc.* v *Gillman, et al.*, Civil Docket No. 3:11-CV-2408-P-BD (N.D. Texas).

Petition for Covered Business Method Review as filed with the United States Patent Trial and Appeal Board in re Post-Grant Review of corresponding U.S. Pat. No. Re. 43,904 on Aug. 19, 2013.

Visa Commercial Solutions: Merchant Category Codes for IRS Form 1099-MISC Reporting, Visa U.S.A. Inc., 2004.

* cited by examiner

PAYMENT CARD RECONCILIATION BY AUTHORIZATION CODE

PRIORITY CLAIM

This application is a continuation of, and claims priority to, U.S. Non-provisional patent application Ser. No. 16/914,600, filed Jun. 29, 2020, entitled "Payment Card Reconciliation by Authorization Code," which is a continuation of, and claims priority to, U.S. Non-provisional patent application Ser. No. 15/131,742, filed Apr. 18, 2016, entitled "Payment Card Reconciliation by Authorization Code," which is a continuation of, and claims priority to, U.S. Non-provisional patent application Ser. No. 14/843,508, filed Sep. 2, 2015, entitled "Payment Card Reconciliation by Authorization Code," which claims priority to U.S. Provisional Patent Application Ser. No. 62/044,446, filed Sep. 2, 2014, entitled "Payment Card Reconciliation by Authorization Code," by the same inventors.

BACKGROUND OF THE INVENTION

1. Field of the Invention

This invention relates to payment processing. More specifically, it relates to facilitating the reconciliation of virtual card payments to 835 remittance advice files using an authorization code generated in the authorization process of the payment card transaction.

2. Background of the Art

The Health Insurance Portability and Accountability Act of 1996 (HIPAA) regulates the use and disclosure of Protected Health Information (PHI) held by "covered entities" (generally, health care clearinghouses, employer sponsored health plans, health insurers, and medical service providers that engage in certain transactions.) The ASC X12N 835 transaction (EDI 835 transaction set) is HIPAA mandated instrument by which electronic healthcare claim payment/advice must be reported.

The EDI 837 transaction set is the format established to meet HIPAA requirements for the electronic submission of healthcare claim information. The claim information included amounts to the following, for a single care encounter between patient and provider: (1) a description of the patient; (2) the patient's condition for which treatment was provided; (3) the services provided; and (4) the cost of the treatment. This transaction set is sent by the providers to payers, which include insurance companies, health maintenance organizations (HMOs), preferred provider organizations (PPOs), or government agencies such as Medicare, Medicaid, etc. These transactions may be sent either directly or indirectly via clearinghouses. Health insurers and other payers send their payments and coordination of benefits information back to providers via the EDI 835 transaction set.

When a healthcare service provider submits an 837 health care claim, the insurance plan uses the 835 to detail the payment to that claim, including what charges were paid, reduced or denied. The 835 is important to healthcare providers, to track what payments were received for services they provided and billed.

Although the 835 can transmit only remittance advice (EOB) it is often used in conjunction with remittance checks and more particularly, ACH electronic payments. For practice management software, the cycle of 837 files (outgoing payment requests) to 835 files (incoming payment advice) calls for associating the 837 and 835 data together for reconciliation and billing. However, in addition to checks and ACH transfers a new technology for payment was recently developed.

Applicant developed a process described in U.S. Pat. No. 7,792,686, (succeeded by RE43904 and RE44748) the specification of which is incorporated herein by reference. The '686 patent discloses a method to deploy a virtual payment card to pay medical service claims. Since there is a one-to-one relationship between the payment card and the specific claim, reconciling the payment is made substantially more efficient. However, within the healthcare space, practice management software by numerous vendors look for the data in the 835 to line up with the data previously sent in the 837 file format. When accepting a virtual payment card as payment for a claim a new issue arises . . . how to link that payment card transaction with the 837 claim file, the 835 remittance advice and the merchant account statement for the healthcare provider.

A need exists in the art for a method to convey virtual card payment transaction data in the 835 remittance file.

SUMMARY OF THE INVENTION

A payment processor acting on behalf of a third party administrator (TPA) to make payment on an adjudicated claim makes a straight through payment to an acquirer for a health care provider's merchant account. Via the settlement process of a straight through payment made between payment processor and the acquirer for the health care provider's merchant account, the payment processor generates an authorization code which is returned to the health care provider on its merchant statement for the payment. An authorization code is a numerical or alphanumerical code sent directly by a credit card issuer or issuing bank that is uniquely ascribed to a sales transaction as verification that the completed sale has been authorized.

Concurrently, the remittance advice from the third party administrator is linked to the same authorization code as the payment by the payment processor which sends the advice in an 835-formatted transmission to the health care provider. Thus, the remittance advice may be linked (reconciled) with the payment on the merchant statement by the common authorization code.

In an embodiment of the invention, a payment processor computing system operating on a computing device receives a data file by a secure FTP transfer from a remote administrator computer to pay an adjudicated claim in an authorized amount to the healthcare provider. The data file includes remittance advice for the claim previously submitted by the healthcare provider which is typically filed in an 837 claim transaction set format.

The payment processor computing system electronically requests a virtual payment card account from a card issuing application in an amount equal to the authorized amount for payment of the claim to the healthcare provider and sends the virtual payment card account data to a payment card acquirer for the healthcare provider of the claim. Data includes the healthcare provider tax identification number, virtual card account number, card expiration date and CVV security code. The payment card acquirer electronically requests authorization from a card network for the virtual payment card data in an amount equal to the authorized amount for the claim. The payment processor computing system directs the generation of an authorization code for the virtual payment card authorization request. In one embodiment of the invention, the authorization code may be randomly generated and then inserted into the 835-format remittance advice file to be sent to the healthcare provider. Another embodiment uses the claim identifier of the 837 claim transaction set or a transaction set code itself as a plug-in value for the authorization code. It is also anticipated that the 837 claim code or transaction code could be a portion or a seed value for the authorization code.

The 835-format remittance advice file is sent from the payment processor computing system to the healthcare provider, the remittance advice file includes the authorization code, whereby the authorization code links funds received through the virtual payment card transaction to the 835 file wherein the healthcare provider may reconcile the payment received through the virtual payment card transaction with the 835 remittance advice file. In an embodiment of the invention, practice management software operated by the healthcare provider imports an electronic 835-format remittance advice file and also imports merchant account statement data which includes the virtual payment card deposit having the authorization code wherein the practice management software automatically links the 835 file with the merchant account statement deposit thereby highly automating both reconciliation and billing to the patient of any unpaid amounts.

In an alternative embodiment of the invention, the payment processing computing system sends both remittance advice and the virtual payment card data to the healthcare provider itself instead of using a straight through transaction to the provider's merchant acquirer. In this embodiment, the healthcare provider keys in the virtual payment card data (e.g., account number, expiration date, CVV value) into a merchant card terminal device. However, the remittance advice send already has the authorization code set by the payment processing computing system. When the virtual payment card issuing authority receives a request for an authorization response via a card network connection (e.g., MASTERCARD, VISA) the authority will send the authorization code already predefined by the payment processing computing system so that the merchant card statement of the healthcare provider will show the virtual card payment deposit in association with an authorization code that matches the data on the remittance advice previously received.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention relates to reconciling virtual payment card transactions with remittance advice (or explanation of benefits). Both credit card data and health care data are highly sensitive and subject to differing security requirements. A technology disclosed in U.S. Pat. No. 8,249,893 (incorporated herein by reference) by the same inventor teaches a process for effecting straight through payment transactions for adjudicated health care provider claims wherein the acquirer of the health care provider's merchant account is paid directly without any intervention by the health care provider. In such case, the remittance advice still must be sent to the health care provider to identify what was approved or denied according to the applicable insurance coverage.

The present invention takes advantage of the opportunity to generate a unique authorization code upon the settlement of the straight through transaction and then link the remittance advice with that same authorization code. Thus, the merchant statement received by the health care provider listing payments has an authorization code that is separately tied to the remittance advice file.

This feature advances the state of the art by minimizing the transmission of sensitive payment card data to the office of the health care provider. The acquirer of the merchant account for the health care provider receives the payment directly minimizing the possibility for fraud. Nevertheless, by linking the authorization code generated in the settlement of this transaction to the explanation of benefits, the health care provider can reconcile it to payment already received and enumerated on the merchant statement received by the health care provider.

Figure 1:
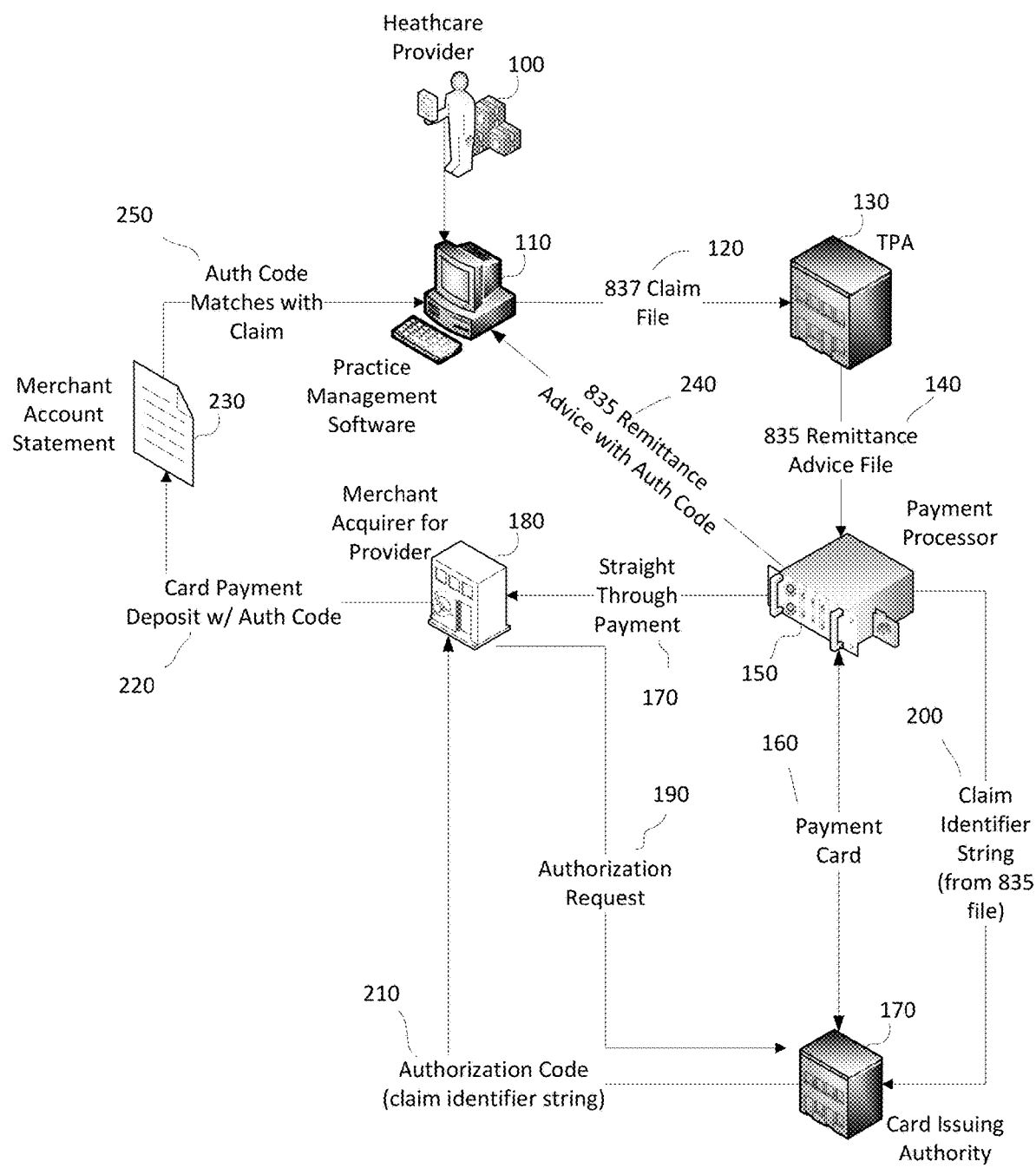
FIG. 1 is a diagrammatic view of an embodiment of the invention.

Turning to FIG. 1, healthcare provider 100 using practice management software 110 generates and transmits 837 claim file 120 to an insurer where it is evaluated by third party administrator (TPA) 130. By way of example, practice management software is sold under the following brands: EPIC, ATHENAHEALTH, ECLINICALWORKS, NEXTGEN, MCKESSON, GE HEALTH, GREENWAY and ALLSCRIPTS.

TPA 130 adjudicates the 837 claim file 120 and determines what payments are due provider 100. TPA 130 generates an 835 remittance advice file 140 which is also known as an explanation of benefits (EOB), explanation of payment (EOP) and/or electronic remittance advice (ERA). In an alternatively embodiment of the invention, TPA 130 simply provides the underlying data for the 835 file but the actual construction of the file is done by payment processor 150. Payment processor 150 is a computer or collection of network computers that direct a number of processes and functions. Processor 150 parses the ASCII 835 file for string, decimal and integer values that collectively identify the payee, the claim description, the benefits payable and the claim identifier set by practice management software 110 and included in the initial 837 claim file 120.

Payment process 150 requests a virtual payment card 160 from a virtual card issuing authority 170. The card issuing authority 170 may be a separate entity from processor 150 or within the same operation. Card issuing authority 170 generates a virtual card account 160 for the amount authorized by TPA 130.

The virtual card account 160 cannot be charged for an amount greater than that authorized by TPA 130 in the 835 remittance advice file 140. The virtual card account 160 is transmitted as a straight through payment 170 to merchant acquirer 180 for the provider. A merchant acquirer is a bank or financial institution that processes credit or debit card payments on behalf of a merchant. The term acquirer indicates that the bank accepts or acquires credit card payments from the card-issuing banks within an association.

Acquirer 180 sends an authorization request 190 to card issuing authority 170 to check that valid credit exists. As the virtual payment card 160 has already been approved for the TPA 130 authorized amount by payment processor 150, the transaction for the authorization amount will be approved by card issuing authority 170 provided there are no anomalies in the authorization request 190 (e.g., data that might indicate fraud or theft).

Prior to the invention herein, an authorization code would be sent by card issuing authority 170 with a character code (typically integers) that relate to the status of the authorization (approved, declined, etc.). In the present invention, payment processor 150 sends card issuing authority 170 claim identifier string 200 obtained from the 835 which may also have originated from the 837 claim file 120 and uses identifier string 200 (or a derivative thereof) as authorization code 210. The virtual card payment is deposited 220 and the deposit transaction is linked with the authorization code 210 which correlates with the claim identifier 200, 835 remittance advice file 140 and the 837 claims file 120. When provider 100, using practice management software 110 imports a merchant account statement 230 containing the payment card deposits, each deposit also has the authorization code 210 which links to 835 remittance advice file 240 sent by payment processor 150. Practice management software 110 matches 250 the authorization code of the deposit 220, the 835 remittance advice file 240 and the original 837 claim file 120. Once matched, practice management software 110 can reconcile that the claim 120 was adjudicated and paid. Typically, a portion of the 837 claim amount is authorized for payment so practice management software 110 can then initiate functions to invoice patients for amounts not paid (e.g., patient responsibility).

Figure 2:
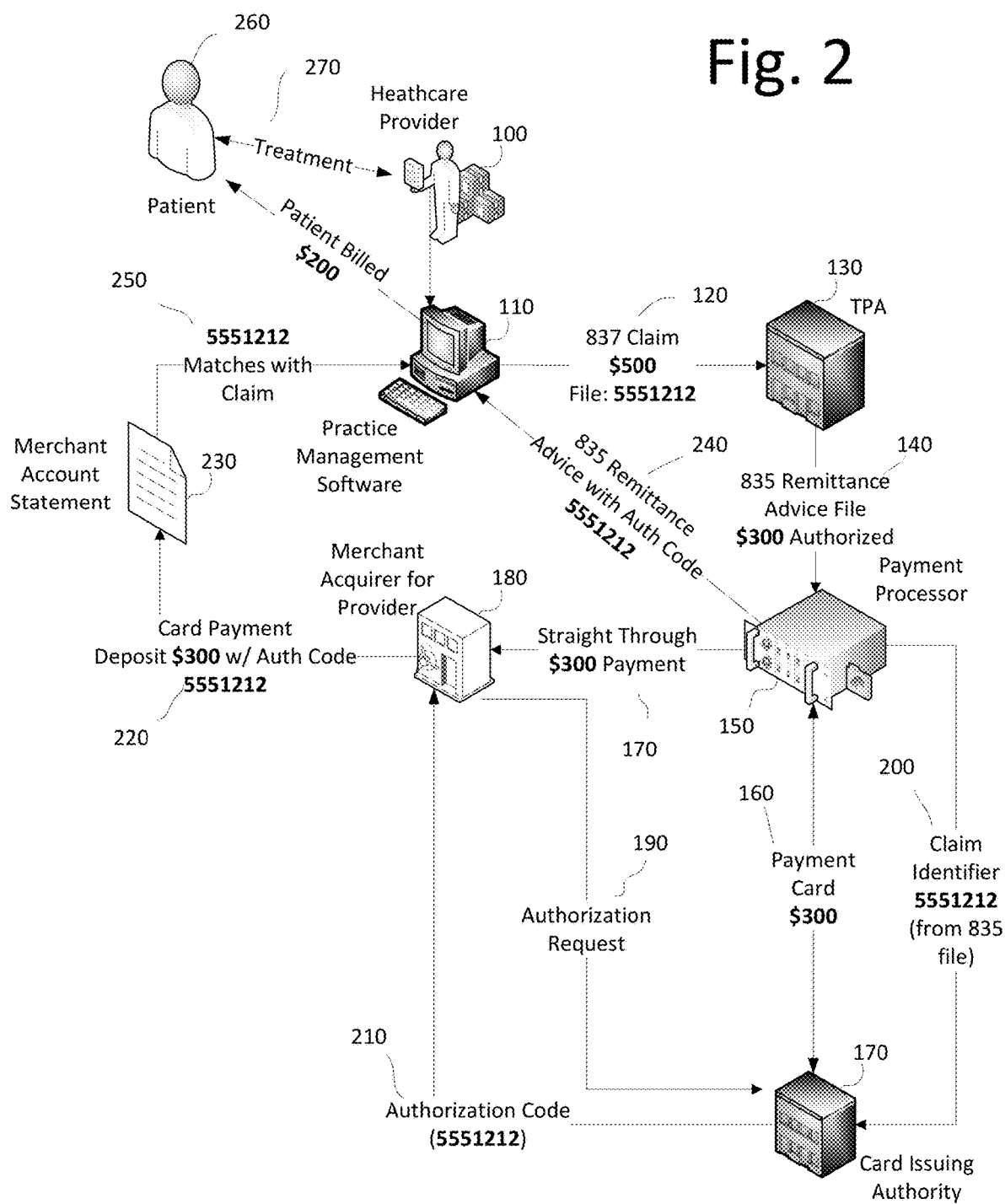
FIG. 2 is a diagrammatic view of the embodiment of the invention in FIG. 1 with an exemplary claim identifier and payment amount shown.

In FIG. 2, an exemplary claim amount ($500) and claim identification (5551212) is employed to demonstrate an embodiment of the invention. Healthcare provider 100 provides treatment 270 to patient 260 and, using practice management software 110, generates an 837 claim file 120 under a claim identification value of 5551212 for an amount of $500. TPA 130 adjudicates the 5551212 claim and finds that $300 should be covered under a policy of patient 260 and $200 should be denied coverage. TPA 130 generates 835 remittance advice file 140 authorizing payment of $300 to healthcare provider 100. Payment processor 150 receives the 835 remittance advice file 140 and directs that a virtual payment card account 160 be generated for $300 by card issuing authority 170. Payment processor also passes on claim identifier 200 from the 835 remittance advice file 140 to card issuing authority 170. When straight through payment 170 is made for $300 to merchant acquirer for provider 180, authorization request 190 to card issuing authority 170 returns an authorization code 210 of 5551212 which reflects in the deposit statement 230 for healthcare provider 100. Practice management software 110 matches the 5551212 from the card merchant account to the 835 remittance advice 240 and the original 837 claim file 120 and subtracts the 837 claim file 120 amount ($500) from the card payment amount deposit 220 ($300) authorized by TPA 130 and, in turn, bills patient 260 for his patient responsibility of $200.

Figure 3:
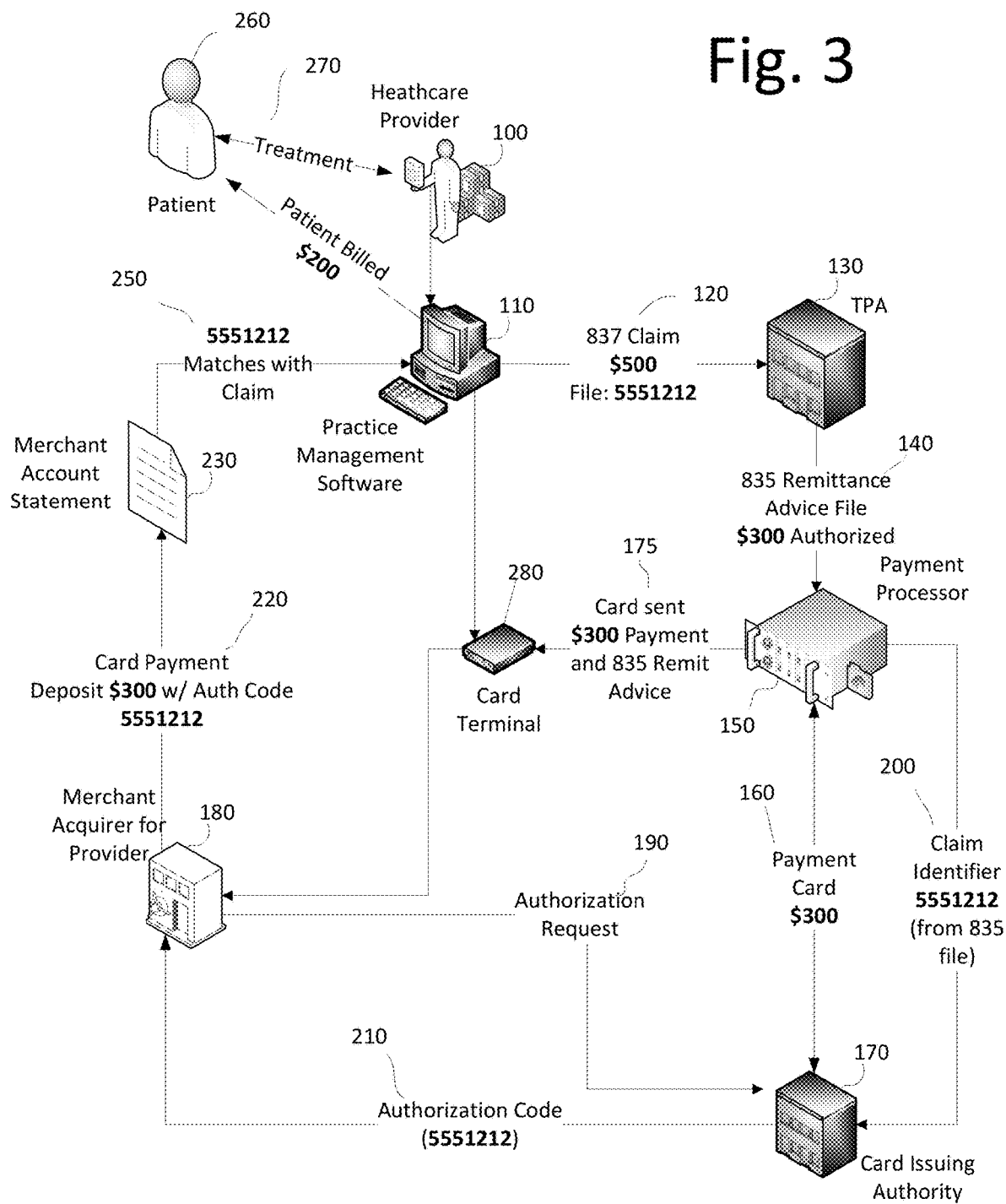
FIG. 3 is a diagrammatic view of an alternative embodiment of the invention using a payment terminal.

FIG. 3 shows an alternative embodiment of the invention in which payment processor 150 does not submit a straight through transmission of the virtual payment card 160 to merchant acquirer 180. Rather, payment processor sends both the virtual card account data and the 835 remittance advice together 175 to provider 100 who then processes the virtual card account on a card terminal 280. The card terminal 280 send the virtual card account data (including account number, amount, expiration date and CVV security code) to merchant acquirer 180 for the provider. Responsive to the authorization request 190, card issuing authority 170 sends back authorization 210 which is linked to the identity of the 837 claim file 120 and associated 835 remittance advice file 140. The authorization code (5551212) shows up associated with the payment on the merchant account statement 230 which practice management software 110 uses to reconcile the 837, 835 and its merchant account statement together and then properly bill patient 260 for the non-covered amount.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

GLOSSARY OF CLAIM TERMS

Authorization Approval Code: an alphanumeric code (typically six or seven-digits) assigned by the issuer to identify the approval for a specific authorization request. Also referred to as "issuer's response code." "authorization approval code" or "authorization response code."

Bank Account Information: information used to identify a specific bank account. This information can include routing numbers, account data, account numbers and other information used to identify a bank account.

BIN: is a six-digit Bank Identification Number assigned to each federally insured financial institution for the routing of transactions and other purposes. It is also known as an Issuer Identification Number (IIN) the first digit of which is the Major Industry Identifier (MII).

Card Association: a collective network of both the card network and the banks that issue cards operable on the network's infrastructure.

Card Network: financial networks that administer the credit and debit card processing. These networks include those known by the brands VISA, MASTERCARD, AMERICAN EXPRESS, DISCOVER, DINER'S CLUB, and JCB.

Card Verification Code (CVV): is numeric security code that provides extra security against unauthorized use during non-face to face transactions. CVV codes are three-digit numbers on the back of VISA and MASTERCARD credit and debit cards. The CVV number helps guard against the use of data stolen from payment networks by hackers. Intercepted data will usually comprise the cardholder name, card number and card expiration date, but not the CVV, which is generally obtained only by viewing the physical card.

CNP Transaction: is a "card not present" transaction such as payments taken over the Internet or by phone or mail.

Computer Based Server: a computer hardware system dedicated to running one or more services. Services can vary from database server, file server, mail server, print server, web server, or various other types services achieved through a computer program.

Computing Device: a computer hardware system typically connected by a wide area or local area network to transmit data, receive data, and store (either ephemerally or permanently)_said data in conjunction with its programming Computing device may also perform business logic, calculations, and present data by various media.

Data file: is a computer file which stores data to be used by a computer application or system.

Digital storage medium: is any data repository able to save non-transitory information. This is typically or more hard drives operable by a relational database.

EDI: Electronic Data Interchange.

EFT: Electronic Funds Transfer.

Electronic Remittance Advice (ERA): Any of several electronic formats for explaining the payments of health care claims.

Enhanced Data: Additional data submitted by a merchant through a credit card network that typically lowers the interchange rate incurred for the transaction. Enhance data includes sales tax breakdown, customer references, merchant order numbers, transportation information, hotel accommodation information, car rental data, product codes, item descriptions, item quantities, item units, discount amounts, shipping information and the like. This additional data is known as Level II and Level II data.

Explanation of benefits (EOB): is a statement typically sent by a health insurance entity explaining what medical services were covered under an insurance policy. An EOB will typically include a summary of the services performed, the medical provider's fee and the amount a patient is responsible for.

Fax: is short for facsimile. It is a method of sending image data across the standard phone line to another fax machine. It is considered by many service providers a relatively secure means of transmitting and receiving sensitive financial and medical information.

FTP: (file transfer protocol) is an Internet protocol is used to copy files between computers—usually a client and an archive site. For the purposes of this application this includes encrypted variants such as Explicit FTPS, SSH File Transfer Protocol and tunneling a normal FTP session over an SSH connection.

Healthcare Claim: refers to an electronic transition standard code 837 as defined by X12. Variants of the 837 code include 837i for institutional health care claims; 837p for professional health care claims; and 837d for dental health care claims.

Healthcare Claim Payment (835): refers to an electronic transition standard code 835 as defined by X12 for a health care claim payment and remittance advice.

Healthcare Providers: include physicians, dentists, pharmacists, physician assistants, nurses, and the like. Providers may also include the hospitals, clinic and institutions themselves for the purposes of claim interpretation.

IIN: a six-digit Issuer Identification Number (IIN) (also known as the "Bank Identification Number" (BIN)) the first digit of which is the Major Industry Identifier (MII).

Independent Sales Organization (ISO): A company or individual contracted with a payment card processor or acquirer to acquire new merchants. Many ISOs provide customer support, technical support and installation support to its customers on behalf of the acquirer.

Interchange Fee: the fee paid between banks for the acceptance of credit and/or debit card based transactions. The interchange rate may be greater for certain transactions including, but not limited, those wherein the physical card is not present at the point-of-sale card terminal.

Issuing Bank: the bank that issues a credit, debit or stored value card to a consumer. This may be synonymous with the card processor in the context of the current claims. This is typically the cardholder's financial institution but in the case of a payment processor, the issued cards may be that of the processor.

Message: generally means an object of communication or vessel which provides information.

Payee: is the recipient of the payment card funds. In health care, this may be the service provider (e.g., physician's office).

Payor: In health care, an entity that assumes the risk of paying for medical treatments. This can be an uninsured patient, a self-insured employer, or a health care plan or HMO.

Payment Card: refers to any credit card, debit card, stored value card or the like.

Payment Card Acquirer (or merchant acquirer): is a bank or financial institution that processes credit or debit card payments on behalf of a merchant. The term acquirer indicates that the bank accepts or acquires credit card payments from the card-issuing banks within an association.

Payment Processor Computing System: is one or more computers communicatively coupled to operate as a special-function device according to computer-readable software instructions stored on a media accessible by the system. Computing systems will include the computer along with any software and peripheral devices that are necessary to make the computer function. Every computer system, for example, requires an operating system. The system is typically communicatively coupled to remote entities such as third party administration systems, card issuing authorities and the like.

Payment Receipt: refers to a transmission made by fax, email, or the like confirming that a direct payment has been made from the card processor to the acquirer for the service provider's merchant account. The payment receipt may be a merger of an authorization code, amount paid, date of payment, payer identity and an explanation of benefits into a single file or document.

Personal Information: information that can be used to uniquely identify, contact, or locate a single person or can be used with other sources to uniquely identify a single individual.

Remote administrator: is a payor or designated authority for the payor such as a third party administrator that adjudicates claims.

PCI DSS: is an acronym for the payment card industry data security standard. PCI DSS is a security standard for organizations that handle cardholder information.

Service Provider: refers to the entity that provides services to be paid for. Service providers applicable to the current invention may include, but are not limited to, construction contractors, vehicle repair shops, pharmacies and medical service providers.

Standard Industrial Classification (SIC) code: is a United States government system for classifying industries by a four-digit code. This is also known as a Merchant Category Code (MCC).

Storage Device: is an electronic storage medium such as a hard drive, hard drive array, solid state memory, magnetic tape, and optical drives.

Stored Value Card: are those payment cards (in tangible or virtual form) which have a monetary value stored on them. Whereas the prepaid credit card can only be used with authorization from the cardholder, the stored value cards have an anonymous aspect. Examples of stored-value cards include the well-known telephone cards, merchant gift cards, or prepaid debit cards.

Tax Identification Number: is an identifying number used for tax purposes in the United States. It is also known as a Taxpayer Identification Number (TIN) or Federal Taxpayer Identification Number. A TIN may be assigned by the Social Security Administration or by the Internal Revenue Service (IRS).

Virtual Payment Card: are payment cards that are generated electronically and not reduced to a physical plastic card. Virtual payment cards may be processed by a service provider as a CNP transaction or the data may be transmitted directly to the card acquirer for the service provider which in such case the CNP designation may or may not be included.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A computer-implemented method comprising:
receiving, by one or more processors of a payment processor computing system and over a computer network, a data file comprising (1) instructions to pay one or more adjudicated claims in an authorized amount to a healthcare provider having a unique identifier, and (2) a remittance advice file originating in response to one or more claims previously submitted by the healthcare provider;
electronically requesting, by the one or more processors and from a payment issuing authority, electronic payment data for the authorized amount corresponding to the one or more adjudicated claims;
electronically sending, by the one or more processors and to a merchant acquirer for the healthcare provider, the unique identifier and the electronic payment data;
generating, by the one or more processors, an authorization code for an electronic payment authorization request associated with the data file;
setting, by the one or more processors, the authorization code to a claim identifier value provided in the one or more claims previously submitted by the healthcare provider, wherein an authorization response associated with the electronic payment authorization request includes the claim identifier value as the authorization code;
generating, by the one or more processors, a modified remittance advice file by inserting the authorization code into the remittance advice file; and
electronically sending, by the one or more processors and to the healthcare provider, the modified remittance advice file, wherein the authorization code links funds received through an electronic payment transaction to the modified remittance advice file such that the healthcare provider can automatically reconcile a payment received through the electronic payment transaction with the modified remittance advice file.

2. The computer-implemented method of claim 1, further comprising:

electronically sending, by the one or more processors, the claim identifier value as the authorization code to the payment issuing authority such that the payment issuing authority can include the claim identifier value as the authorization code in the authorization response to the merchant acquirer electronically requesting authorization from the payment issuing authority.

3. The computer-implemented method of claim 1, wherein the electronic payment data is configured to be charged an amount equal to the authorized amount for payment of the one or more adjudicated claims.

4. The computer-implemented method of claim 1, wherein the unique identifier comprises a tax identification number.

5. The computer-implemented method of claim 1, wherein the electronic payment data is sent to the healthcare provider instead of the merchant acquirer so that the healthcare provider can electronically request authorization for the electronic payment data in an amount equal to the authorized amount to be paid to the healthcare provider for the one or more adjudicated claims.

6. The computer-implemented method of claim 1, wherein the electronic payment data comprises a virtual payment card.

7. The computer-implemented method of claim 1, wherein the remittance advice file and the modified remittance advice file are in a first format and the one or more claims previously submitted by the healthcare provider are in a second format.

8. A system comprising one or more processors and at least one memory storing processor executable instructions that, when executed by the one or more processors, cause the one or more processors to perform operations comprising:

receiving, over a computer network, a data file comprising (1) instructions to pay one or more adjudicated claims in an authorized amount to a healthcare provider having a unique identifier, and (2) a remittance advice file originating in response to one or more claims previously submitted by the healthcare provider:

electronically requesting, from a payment issuing authority, electronic payment data for the authorized amount corresponding to the one or more adjudicated claims;

electronically sending, to a merchant acquirer for the healthcare provider, the unique identifier and the electronic payment data:

generating an authorization code for an electronic payment authorization request associated with the data file;

setting the authorization code to a claim identifier value provided in the one or more claims previously submitted by the healthcare provider, wherein an authorization response associated with the electronic payment authorization request includes the claim identifier value as the authorization code:

generating a modified remittance advice file by inserting the authorization code into the remittance advice file; and electronically sending, to the healthcare provider, the modified remittance advice file, wherein the authorization code links funds received through an electronic payment transaction to the modified remittance advice file such that the healthcare provider can automatically reconcile a payment received through the electronic payment transaction with the modified remittance advice file.

9. The system of claim 8, wherein the processor executable instructions further cause the one or more processors to perform operations comprising:

electronically sending the claim identifier value as the authorization code to the payment issuing authority such that the payment issuing authority can include the claim identifier value as the authorization code in the authorization response to the merchant acquirer electronically requesting authorization from the payment issuing authority.

10. The system of claim 8, wherein the electronic payment data is configured to be charged an amount equal to the authorized amount for payment of the one or more adjudicated claims.

11. The system of claim 8, wherein the unique identifier comprises a tax identification number.

12. The system of claim 8, wherein the electronic payment data is sent to the healthcare provider instead of the merchant acquirer so that the healthcare provider can electronically request authorization for the electronic payment data in an amount equal to the authorized amount to be paid to the healthcare provider for the one or more adjudicated claims.

13. The system of claim 8, wherein the electronic payment data comprises a virtual payment card.

14. The system of claim 8, wherein the remittance advice file and the modified remittance advice file are in a first format and the one or more claims previously submitted by the healthcare provider are in a second format.

15. One or more non-transitory computer-readable storage media storing processor-executable instructions that, when executed by one or more processors, cause the one or more processors to perform operations comprising:

receiving, over a computer network, a data file comprising (1) instructions to pay one or more adjudicated claims in an authorized amount to a healthcare provider having a unique identifier, and (2) a remittance advice file originating in response to one or more claims previously submitted by the healthcare provider:

electronically requesting, from a payment issuing authority, electronic payment data for the authorized amount corresponding to the one or more adjudicated claims:

electronically sending, to a merchant acquirer for the healthcare provider, the unique identifier and the electronic payment data:

generating an authorization code for an electronic payment authorization request associated with the data file:

setting the authorization code to a claim identifier value provided in the one or more claims previously submitted by the healthcare provider, wherein an authorization response associated with the electronic payment authorization request includes the claim identifier value as the authorization code:

generating a modified remittance advice file by inserting the authorization code into the remittance advice file; and electronically sending, to the healthcare provider, the modified remittance advice file, wherein the authorization code links funds received through an electronic payment transaction to the modified remittance advice file such that the healthcare provider can automatically reconcile a payment received through the electronic payment transaction with the modified remittance advice file.

16. The one or more non-transitory computer-readable storage media of claim 15, wherein the processor-executable instructions further cause the one or more processors to perform operations comprising:

electronically sending the claim identifier value as the authorization code to the payment issuing authority such that the payment issuing authority can include the claim identifier value as the authorization code in the authorization response to the merchant acquirer electronically requesting authorization from the payment issuing authority.

17. The one or more non-transitory computer-readable storage media of claim 15, wherein the electronic payment data is sent to the healthcare provider instead of the merchant acquirer so that the healthcare provider can electronically request authorization for the electronic payment data in an amount equal to the authorized amount to be paid to the healthcare provider for the one or more adjudicated claims.

18. The one or more non-transitory computer-readable storage media of claim 15, wherein the electronic payment data comprises a virtual payment card.

19. The one or more non-transitory computer-readable storage media of claim 15, wherein the remittance advice file and the modified remittance advice file are in a first format and the one or more claims previously submitted by the healthcare provider are in a second format.

\* \* \* \* \*

UNITED STATES PATENT AND TRADEMARK OFFICE
CERTIFICATE OF CORRECTION

PATENT NO. : 12,260,405 B1
APPLICATION NO. : 17/901409
DATED : March 25, 2025
INVENTOR(S) : Robert M. Allen et al.

Page 1 of 1

It is certified that error appears in the above-identified patent and that said Letters Patent is hereby corrected as shown below:

In the Claims

In Column 10, Line 41, Claim 1, delete "provider:" and insert -- provider; --, therefor.

In Column 10, Line 45, Claim 1, delete "claims:" and insert -- claims; --, therefor.

In Column 10, Line 58, Claim 1, delete "code:" and insert -- code; --, therefor.

In Column 11, Line 45, Claim 8, delete "provider:" and insert -- provider; --, therefor.

In Column 11, Line 51, Claim 8, delete "data:" and insert -- data; --, therefor.

In Column 11, Line 59, Claim 8, delete "code:" and insert -- code; --, therefor.

In Column 12, Line 42, Claim 15, delete "provider:" and insert -- provider; --, therefor.

In Column 12, Line 45, Claim 15, delete "claims:" and insert -- claims; --, therefor.

In Column 12, Line 48, Claim 15, delete "data:" and insert -- data; --, therefor.

In Column 12, Line 50, Claim 15, delete "file:" and insert -- file; --, therefor.

In Column 12, Line 56, Claim 15, delete "code:" and insert -- code; --, therefor.

Signed and Sealed this
Eighth Day of July, 2025

Coke Morgan Stewart
*Acting Director of the United States Patent and Trademark Office*